United States Patent
De Miranda

(12) 
(10) Patent No.: US 6,619,598 B2
(45) Date of Patent: Sep. 16, 2003

(54) ARM SUPPORT EQUIPMENT EASILY ADAPTABLE TO ANY DENTIST CHAIR AND/OR OPERATING TABLE

(76) Inventor: Teresa Elias Chacur De Miranda, Rua Professor Abelardo Lobon 68/301, Lagoa, 22470-240 Rio de Janeiro, RJ (BR)

( * ) Notice: Subject to any disclaimer, the term of this patent is extended or adjusted under 35 U.S.C. 154(b) by 0 days.

(21) Appl. No.: 10/154,928

(22) Filed: May 28, 2002

(65) Prior Publication Data

US 2003/0010875 A1 Jan. 16, 2003

(30) Foreign Application Priority Data

Jul. 13, 2001 (BR) .............................................. 0102885

(51) Int. Cl.$^7$ ................................................ A47C 7/54
(52) U.S. Cl. ............................... 248/118.3; 297/411.23; 297/411.35
(58) Field of Search ........................ 297/411.23, 411.25, 297/411.35, 411.36, 411.37, 411.38, 411.39, 411.4, 411.46; 248/118, 118.1, 118.3; 400/715

(56) References Cited

U.S. PATENT DOCUMENTS

| | | | |
|---|---|---|---|
| 527,056 A | * 10/1894 | Gilson | 297/464 |
| 602,084 A | * 4/1898 | Kjoer | 248/118 |
| 1,516,795 A | * 11/1924 | Schwarting | 5/646 |
| 4,332,263 A | * 6/1982 | Kitrell | 132/73 |
| 4,913,393 A | * 4/1990 | Wood | 248/230.02 |
| 5,407,249 A | * 4/1995 | Bonutti | 297/411.35 |
| 5,462,247 A | * 10/1995 | Aldrich | 248/118 |
| 5,713,591 A | * 2/1998 | Zarkhin et al. | 280/250.1 |
| 6,427,273 B1 | * 8/2002 | Berke et al. | 5/657 |

FOREIGN PATENT DOCUMENTS

DE          672901       * 3/1939 ............ 297/411.37

OTHER PUBLICATIONS

U.S. patent application No. 2002/0109387, Publication date Aug. 15, 2002, filed Feb. 15, 2001, inventor Noiseux, Classification: 297/411.37.*

* cited by examiner

Primary Examiner—Ramon O. Ramirez
Assistant Examiner—Jon Szumny
(74) Attorney, Agent, or Firm—Birch, Stewart, Kolasch & Birch, LLP

(57) ABSTRACT

Arm support equipment for use in connection with a dentist chair and/or operating table, comprising a base (1) capable of being removably attached to the dentist chair and/or operating table, a bar-shaped element having in at least one end thereof a housing (2) provided with fastening means (3), at least one S-shaped linking element (4), at least one latching element (5) including at least one cavity (6) provided with fastening means (7), at least one support means comprising a support surface (8) and a fitting stem (8'), disposed perpendicularly to the support surface (8), wherein one of the ends of the S-shaped linking element (4) is hingedly fitted in the housing (2) provided with the fastening means (3) of the base (1), the other end of the S-shaped linking element (4) being hingedly fitted in a cavity (6) of the latching element (5), the fitting stem (8') being also hingedly fitted in the cavity (6) of the latching element (5).

6 Claims, 4 Drawing Sheets

ARM SUPPORT EQUIPMENT EASILY ADAPTABLE TO ANY DENTIST CHAIR AND/OR OPERATING TABLE

FIELD OF THE INVENTION

The present invention refers to arm support equipment easily adaptable to any dentist chair and/or operating table.

BACKGROUND OF THE INVENTION

In certain situations, such as for example in microsurgery and dental treatments, some medical and/or dental professionals are bound to work for many hours at a time with their arms suspended, practically stationary. This practice, when repetitive, may lead to muscle or tendon fatigue, and might constitute a cause of acute or chronic lesions in the muscle groupings and other soft structures that comprise the joints of the upper limbs of the pectoral girdle.

There is thus a need to provide a special support for the arms allowing easy horizontal and vertical displacement about the work area, in order to reduce static muscle contraction, whereby the arm support equipment reduces muscle fatigue and/or the occurrence of lesions in the structures that integrate the joints of the upper limbs of the pectoral girdle, avoiding a prolonged static suspension posture devoid of support to the muscles involved in the professional activity.

SUMMARY OF THE INVENTION

Therefore, in order to achieve the above objects, there has been provided the arm support equipment easily adaptable to any dentist chair and/or operating table according to the present invention, that is characterized by comprising: a base, removably attached to the dentist chair and/or operating table, comprised by at least one linking element in the shape of an "S"; at least one latching device having at least one cavity with a fastening device; and at least one support device comprising a support surface and a fitting stem, provided perpendicularly to the support surface, wherein: one of the ends of the linking element in the shape of an "S" is hingedly fitted in the housing provided with a fastening device of the base; the other end of the linking element in the shape of an "S" is hingedly fitted in a cavity of the latching device; and the fitting stem of the support device is also hingedly fitted in a cavity of the latching device.

In a preferred embodiment, the arm support equipment according to the present invention further includes a linking element in the shape of a "U", linking a latching device to an additional latching device, to which a support device is hingedly attached by its fitting stem. Preferentially, the above mentioned linking elements are tubular elements.

In another preferred embodiment of the arm support equipment according to the present invention, the base is comprised of a bar-shaped element having at each end thereof a housing provided with a fastening device.

In another preferred embodiment of the arm support equipment according to the present invention, the latching device includes two cavities provided with fastening devices.

Preferentially, the cavities and housings are through holes wherein are fitted the ends of the S-shaped or U-shaped linking elements or the fitting stem of the support device, such elements being attached or secured in the holes by the fastening devices.

BRIEF DESCRIPTION OF THE DRAWINGS

A preferred embodiment of the present invention will be described below for mere illustrative purposes in connection with the attached drawings, wherein.

DESCRIPTION OF THE PREFERRED EMBODIMENT

As may be seen in the attached figures, the arm support equipment according to the present invention comprises a base 1 in the shape of a bar with slightly curved ends. Each end of the base comprises a housing 2 provided with a fastening device 3. In the illustrated embodiment, the housing 2 is a through hole wherein is inserted one end of the S-shaped linking element 4. The S-shaped linking element is a tubular element 4 capable of being both swiveled and moved vertically along the through hole of the housing 2. The S-shaped tubular linking element 4 is secured in the desired position by means of the fastening device 3.

The fastening device 3 may be of any appropriate type, such as of pressure type, spring type, hydraulic type, etc. . . . . In the illustrated embodiment, the fastening device is formed by a screw with a handle that can be screwed in a threaded hole provided in a side wall of the housing 2, perpendicularly to the through hole.

Figure 1:
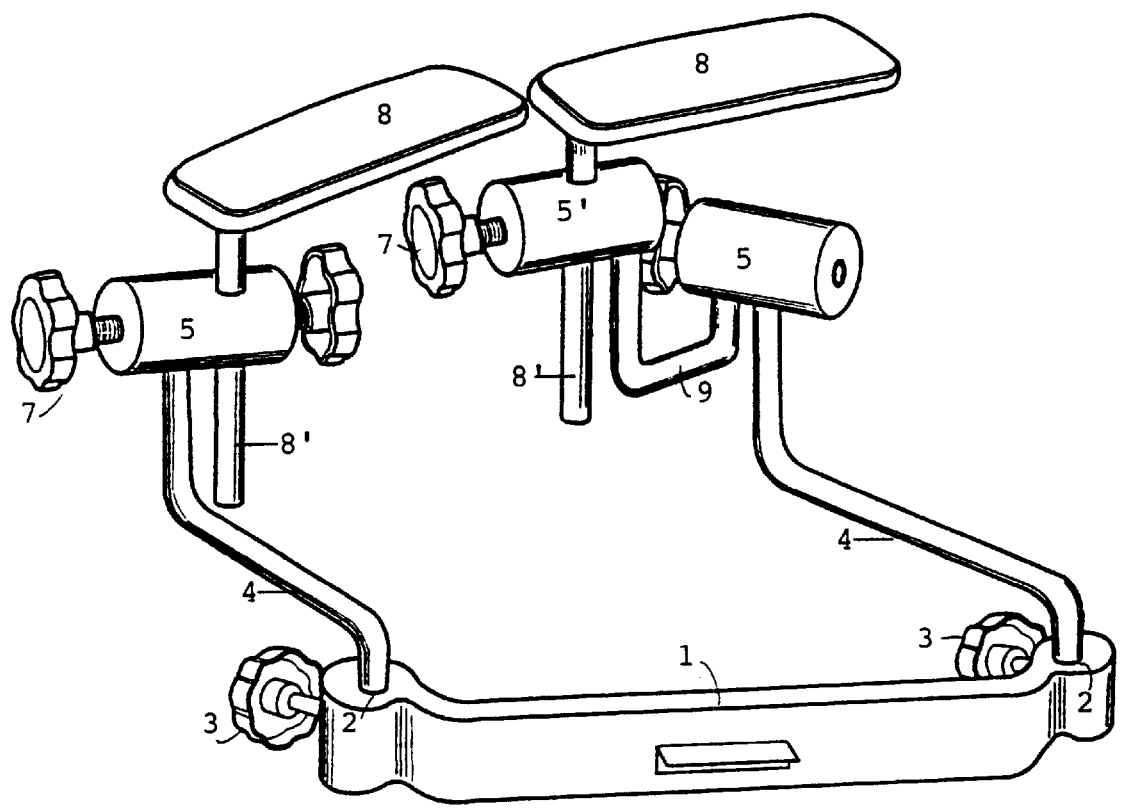
FIG. 1 is a perspective view of the arm support equipment that constitutes the object of the present invention.
Figure 2:
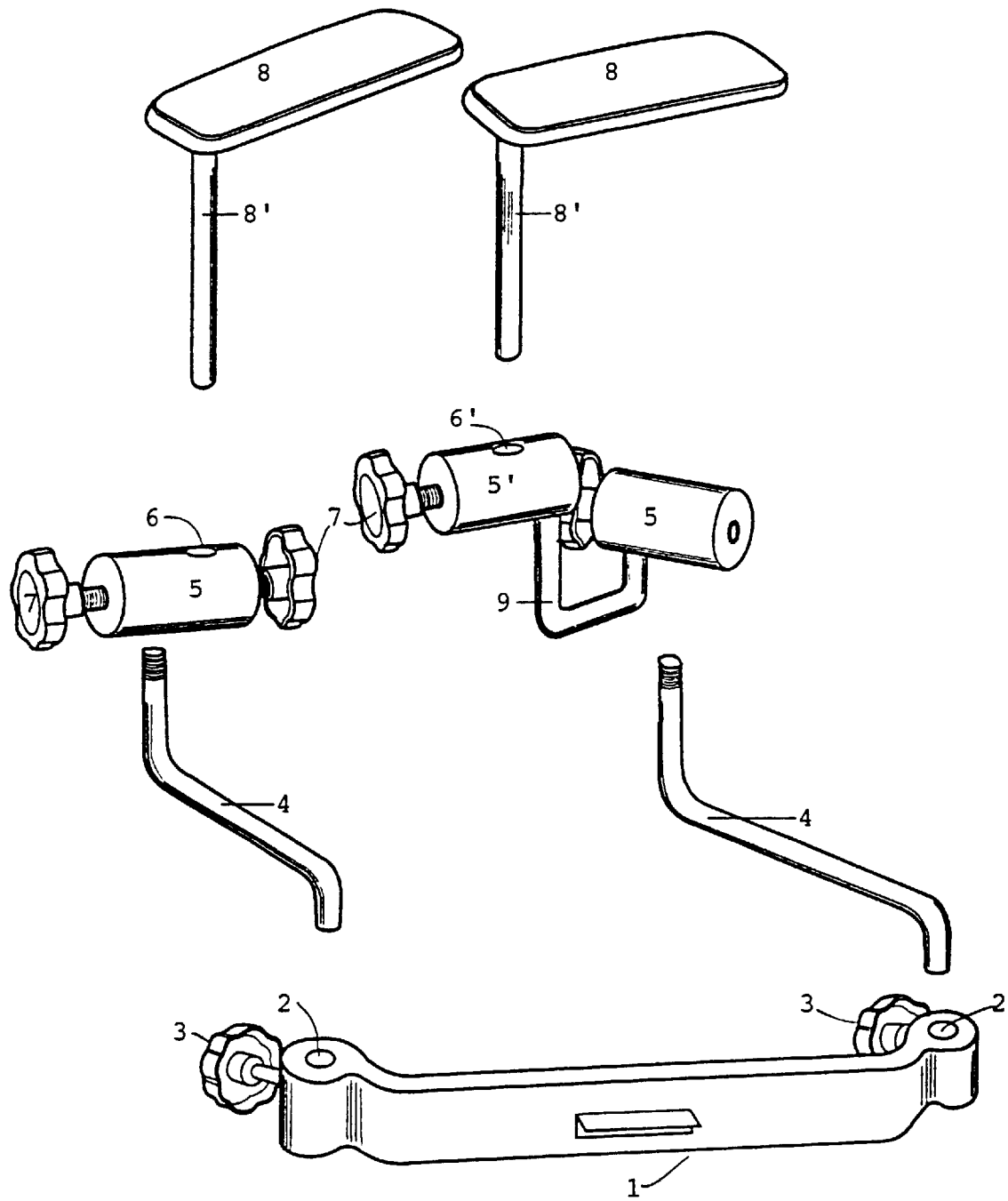
FIG. 2 is an exploded perspective view depicting all the elements that constitute the arm support equipment according to the present invention.
Figure 3:
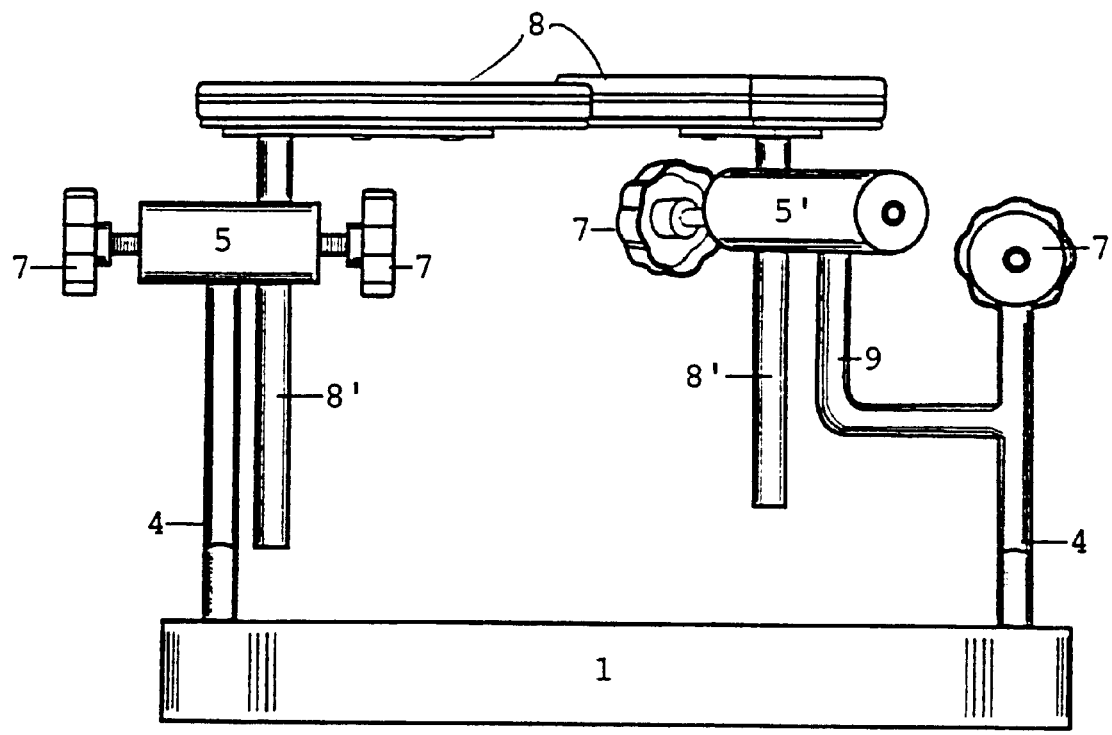
FIG. 3 is a side view of the arm support equipment that constitutes the object of the present invention.
Figure 4:
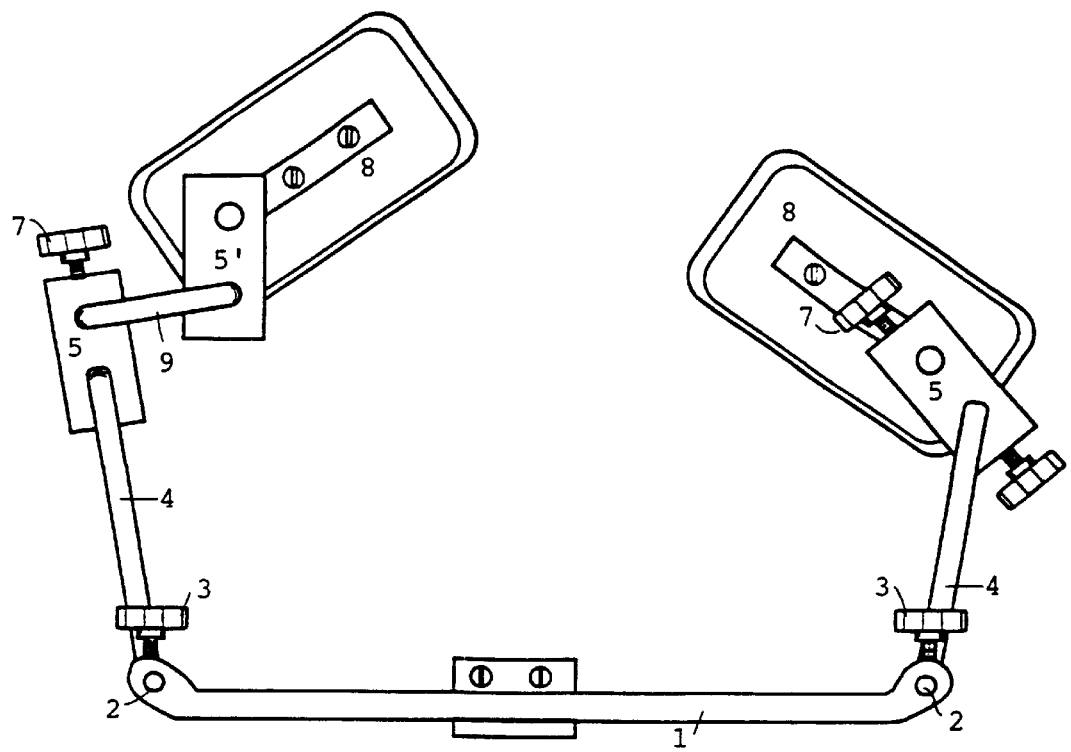
FIG. 4 is a bottom view of the arm support equipment that constitutes the object of the present invention; and, FIG. 5 is a top view of the arm support equipment that constitutes the object of the present invention.
Figure 5:
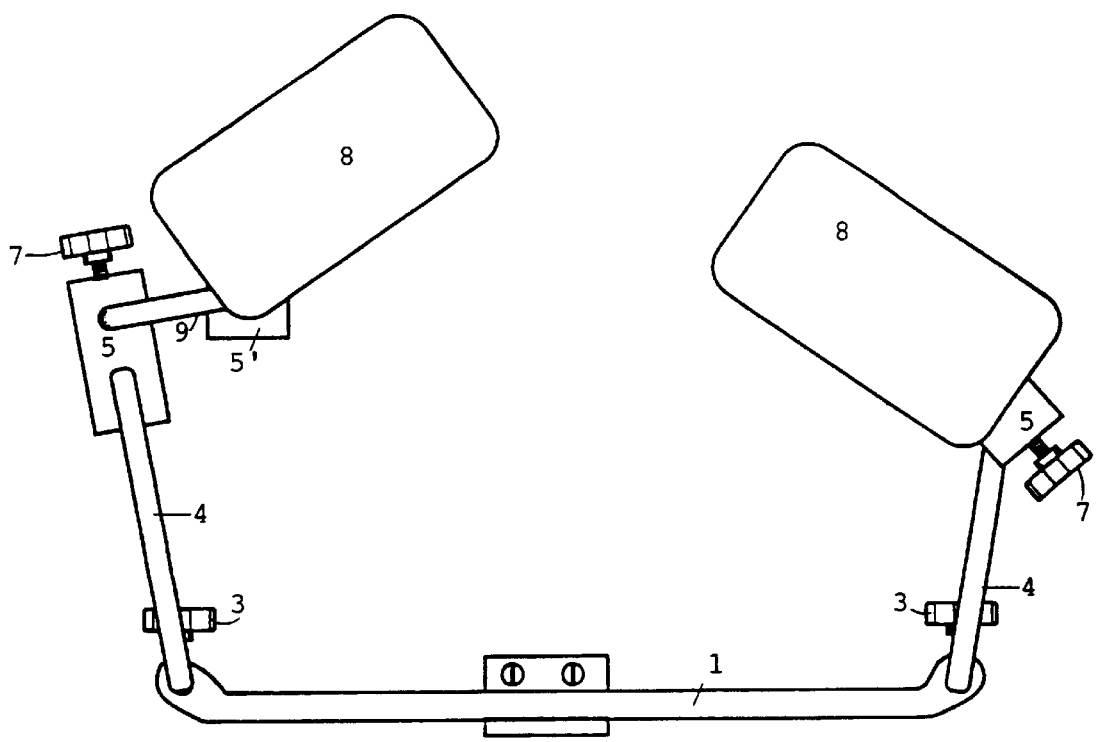

As may be easier to note by referring to FIGS. 1 and 2, specifically regarding the branch shown on the left side of the figures, the opposite end of the S-shaped tubular linking element 4 latches onto the latching device 5. In the illustrated embodiment, the latching device 5 is formed of a cylindrical body provided with two cavities 6, that may or may not be through holes, perpendicular to the longitudinal axis of the cylindrical body, there being provided at each end of the cylindrical body a fastening device 7 similar to the fastening device 3 mentioned above. The latching of the end of the S-shaped tubular linking element 4 is made in one of the cavities or through holes 6 of the latching device 5 and it may be regulated both in swiveling and vertically, being secured in the desired position by the clamping action of the fastening device 7. In the other cavity or through hole 6 of the latching device 5 there is inserted the fitting stem 8' of the support device. As may be seen in detail in FIG. 2, the support device is comprised by a support surface 8 and a fitting stem 8', provided perpendicularly to the support surface 8. The support surface 8 may be lined with a soft material in order to provide additional comfort, there being preferred the use of a denser type of foam material for contact with the arms.

The other branch, the left side one, is in every aspect identical to the right side branch, except in the fact that the connection of the S-shaped tubular linking element 4 with the support device is not provided solely by one latching device 5. In this right-side branch, the connection of the S-shaped tubular linking element 4 with the support device is provided by two latching devices 5 and 5' joined to one another by means of a U-shaped linking element 9, whereby the ends of such linking element, also tubular, in the shape of a "U" are inserted and secured in the cavities or through holes 6 and 6' of the latching devices 5 and 5' exactly in the same manner that the ends of the S-shaped tubular linking element 4 are inserted and secured in the cavities or through holes 6 of the latching device 5.

Although being illustrated in the figures as a cylindrical body provided with two cavities 6, that may be through holes or not, perpendicular to the longitudinal axis of the cylindrical body, having at each end of the cylindrical body a fastening device 7 similar to the fastening device 3, the latching device 5 may have any desired shape, and additionally, it may be comprised of distinct parts joined to one another, such that the parts may be swiveled relatively to one another providing a greater degree of mobility to the equipment in question.

As a rule, the arm support equipment according to the present invention is attached to the dentist chair or the operating table (not shown in the figures) by means of the base 1, which in the illustrated embodiment is provided at the middle region thereof with a screw fastening device. In the case of the dentist chairs, the equipment is preferentially attached between the trunk rest and the headrest.

It is preferred that the arm support equipment easily adaptable to any dentist chair and/or operating table according to the present invention be made of stainless steel, except in the case of the lining of the support surface 8 of the support device, in order to allow the same to be easily cleaned and/or sterilized. However, the components thereof may be made of other appropriate materials.

One such equipment was tested for eight months and there has been evidenced that: it occupies a space without hindering the work environment routines; it may be used in an orthostatic or seated position; it performs its intended function efficiently and it is easy to clean and to maintain; and it accommodates physiological requirements in terms of preservation of the muscle groupings and other soft structures that form the pectoral girdle, by avoiding a prolonged static posture of the muscles involved in the activity.

Furthermore, it has been ascertained that the arm support equipment according to the present invention has an excellent technical, ergonomic and aesthetic quality, and may be used in a preventive fashion to obviate work-related osteomuscular disturbances, and in a corrective fashion as an important aid to treatment, in the case of an already existing lesion.

What is claimed is:

1. Arm support equipment for use in connection with a dentist chair and/or operating table, comprising:
   a base (1) capable of being removably attached to the dentist chair and/or operating table,
   a bar-shaped element having in at least one end thereof a housing (2) provided with fastening means (3);
   at least one S-shaped linking element (4),
   at least one latching element (5) including at least one cavity (6) provided with fastening means (7);
   at least one arm support means comprising a support surface (8) and a fitting stem (8'), disposed Perpendicularly to the support surface (8), wherein one of the ends of the S-shaped linking element (4) is hingedly fitted in the housing (2) provided with said fastening means (3) of said base (1);
   the other end of the said S-shaped linking element (4) being hingedly fitted in a cavity (6) of said latching element (5);
   said fitting stem (8') of the support means being also hingedly fitted in said cavity (6) of said latching element (5)
   a U-shaped linking element (9) linking said latching element (5) to an additional latching element (5') whereby said support means is hingedly attached by said fitting stem (8') to a cavity (6') in said latching element (5').

2. The arm support equipment according to claim 1, wherein the cavities (6) and the housings (2) include through holes.

3. The arm support equipment according to claim 1, wherein the linking elements are tubular elements.

4. The arm support equipment according to claim 1, wherein the base (1) comprises a bar-shaped element having at each end thereof a housing (2) provided with fastening means (3).

5. The arm support equipment according to claim 1, wherein the latching element (5) has two cavities (6) provided with fastening means (7).

6. The arm support equipment according to claim 1, wherein the latching elements (5, 5') comprise distinct portions joined together, so as to allow rotation of said portions relative to one another.

* * * * *